United States Patent [19]
von Reis et al.

[11] Patent Number: 4,561,868
[45] Date of Patent: Dec. 31, 1985

[54] CANISTER FILTER ASSEMBLY

[76] Inventors: Charles von Reis, 1923 Dunmore Rd., Ann Arbor, Mich. 48103; Karlis Vizulis, 202½ W. Henry, Saline, Mich. 48176

[21] Appl. No.: 627,186

[22] Filed: Jul. 2, 1984

[51] Int. Cl.⁴ ............................................ B01D 46/10
[52] U.S. Cl. ........................................ 55/319; 55/327; 55/486; 55/501; 55/DIG. 3
[58] Field of Search ........... 55/332, 333, 159, DIG. 3, 55/486, 501, 503, 505, 318, 319, 320–323, 327

[56] References Cited

U.S. PATENT DOCUMENTS

| | | | |
|---|---|---|---|
| 1,557,592 | 10/1925 | Jones | 446/4 |
| 1,735,441 | 11/1929 | Paffen et al. | 55/311 |
| 2,219,567 | 10/1940 | Spielman | 55/327 |
| 2,226,630 | 12/1940 | McCord | 55/DIG. 3 |
| 2,639,005 | 5/1953 | Gerstmann | 55/DIG. 3 |
| 2,649,927 | 8/1953 | Ortega | 55/332 |
| 3,082,465 | 3/1963 | Wood | 55/DIG. 3 |
| 3,732,075 | 5/1973 | Acaba | 55/321 |
| 4,350,504 | 9/1982 | Diachuk | 55/323 |
| 4,434,564 | 3/1984 | Braggins, Jr. | 55/321 |
| 4,459,139 | 7/1984 | von Reis et al. | 55/159 |

FOREIGN PATENT DOCUMENTS 427468 4/1926 Fed. Rep. of Germany ........ 55/332

Primary Examiner—Tim Miles
Attorney, Agent, or Firm—Reising, Ethington, Barnard, Perry & Milton

[57] ABSTRACT

A canister filter assembly (10) for use in a vacuum line for trapping particulates and liquids from fluid drawn through the vacuum line including a cupped shaped container portion (12) and a lid portion (14) disposed over the container (12) in sealing engagement therewith. The lid (14) includes a fluid inlet (28) and a fluid outlet (30). A filter assembly (16) including a hydrophobic filter (32) and a prefilter (34) filters the particles and aerosols from the fluids passing through the fluid outlet (30). A filter support (18) supports the filters (32, 34, 36) within the filter assembly (16) and includes a cap member (40) spaced below the prefilter (34). The cap member (40) includes an upwardly extending peripheral rim (42) perfecting a seal with the remainder of the filter support (18). The assembly (10) is characterized by the rim (42) including outwardly extending louver portions (50) defining upwardly facing openings (52) proximate to the lid (14) to provide a tortuous path for the entrance of aerosols and particles into the filter support (18).

27 Claims, 3 Drawing Figures

CANISTER FILTER ASSEMBLY

TECHNICAL FIELD

The subject invention relates to a canister filter assembly for use in a vacuum line to remove both liquid and particulate type material from the line.

BACKGROUND ART

Canister assemblies or more generally suction canisters are used as part of a vacuum assembly for the removal of liquids and gases that collect in body cavities because of disease, injury, or surgery. Suctioning may be used to clear passageways, such as tracheal or nasal gastric passageways or may be used in surgical procedures to remove blood and irrigating fluids.

Generally, the assembly includes a vacuum line leading from a motor pump or hospital wall central vacuum system assembly past a valve and gauge for controlling fluid flow therethrough. The line leads to a canister which is a collection mechanism for retaining fluids as a trap to prevent the fluids from being drawn into the motor pump. Patient tubing leads from the canister and may have a suction catheter tip mounted thereon.

The aspirated body fluids may contain infectious viruses and bacteria. If these aerosols or particulates are not trapped within the collection assembly, they can be drawn through the motor pump and into the surrounding environment of the patient and professionals or into the main hospital wall system which can cause contamination, corrosion, and gradual occlusion. Further, aspriation of aerosols through the fluid line and into the motor pump assembly can cause contamination and corrosion of the motor pump.

It is also necessary to prevent overflow of fluid retained in the canister from being drawn up into the suction line and into the motor pump walls. Various mechanisms have been used to prevent this occurrence. For example, a float member may be slidably mounted beneath the vacuum port leading to the motor pump. The float is constructed so that as the fluid volume within the canister rises, the float member perfects a seal against the vacuum port. These mechanisms present several problems. The moving mechanical valve generally is mounted on a post or a group of bosses upon which it slides. The post or bosses may become contaminated so as to cause sticking of the float member. Foaming is another problem which occurs within the canister. Foam rises quickly and may not raise the float while still being aspirated into the fluid line. Such premature shut-off can cause burning out of the vacuum pump motor and more critically, result in ineffective aspiration of a surgical site. At the other extreme, these mechanisms have been caused to prematurely seal the vacuum port by vibration or jarring.

Recently, manufacturers have disposed a filter element within the vacuum port in an attempt to trap the particulate matter escaping therethrough. These filters are retained in a housing wherein there is direct flow of fluid or air into the housing. The housing does not prevent splashing of fluid or foam against the filter. Further, a problem results from impaction of particles against the filter and from the passage of aerosol therethrough. The particles in these prior art systems are drawn forcefully into the canister and against the filter. Impaction of particles and aerosol on the filter decreases flow therethrough.

Other alternative constructions have included crude seals disposed over the vacuum port. An outer plug material having a spiral path extending therethrough and a central plug member disposed within the central portion thereof are used as a filtering device. Such a device is manufactured by Respiratory Care, Inc. of Chicago, Ill.

Various prior art assemblies including filtering mechanisms include filter supports providing a tortuous path for air and aerosols to be drawn through. For example, the U.S. Pat. No. 1,556,592 to Donaldson, issued Oct. 13, 1925 discloses an air cleaner including a filter wherein smoke filled air is drawn into the assembly through a tortuous path. The U.S. Pat. No. 1,735,441 to Paffen et al, issued Nov. 12, 1929 discloses an air compressor assembly wherein air is drawn through a tubing and against a deflector to remove oil droplets from the air prior to being drawing through a filter.

None of the aforementioned prior art assemblies provide means for effectively removing aerosols and particulates from fluid being drawn into a canister or for perfecting an effective seal against overflow of fluid or foam within the container. Aerosol entering into a canister from a lid member has an inertia as it is drawn into the canister. The particles will generally bounce off the sides and bottom of the canister and be deflected towards the vacuum or outlet port also located on the lid of the canister. Prior art filter mechanisms provide no means for effectively removing the aerosols and particulates, and at the same time preventing impaction of these materials directly against the filter material which can cause premature clogging of the filter.

STATEMENT OF THE INVENTION AND ADVANTAGES

According to the present invention, there is provided a canister filter assembly for use in a vacuum line for trapping particulates and liquids from fluid drawn through the vacuum line. The assembly includes a cup-shaped container portion and a lid portion disposed over the container in sealing engagement therewith. The lid portion includes a fluid inlet and fluid outlet. Filter means filter the particulates and liquids from the fluids passing through the fluid outlet. Filter support means supports the filter means within the fluid outlet and includes cover means spaced below the filter means for forcing the flow of fluid into the filter support means downwardly away from the filter means prior to flowing in the opposite direction through the filter means.

This construction prevents the outlet of aerosols into the filter support means that have directly entered the canister, deflected off a wall, and with the strong inertial force created thereby from directly impacting upon the filter medias. Rather, the subject construction forces a downward tortuous path of travel away from the filter means for the aerosols and particulates entering the filter support means. Additionally, the cover means provides additional deflection of the aerosol particulates thereby further decreasing the inertial force of the aerosols and particulates without significantly effecting gas flow through the filter assembly. The result is that gases are effectively and efficiently filtered through the assembly while aerosols and particulates are more effectively trapped within the canister assembly prior to coming in proximity of the filter means, extending filter life.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE DRAWINGS

Figure 1:
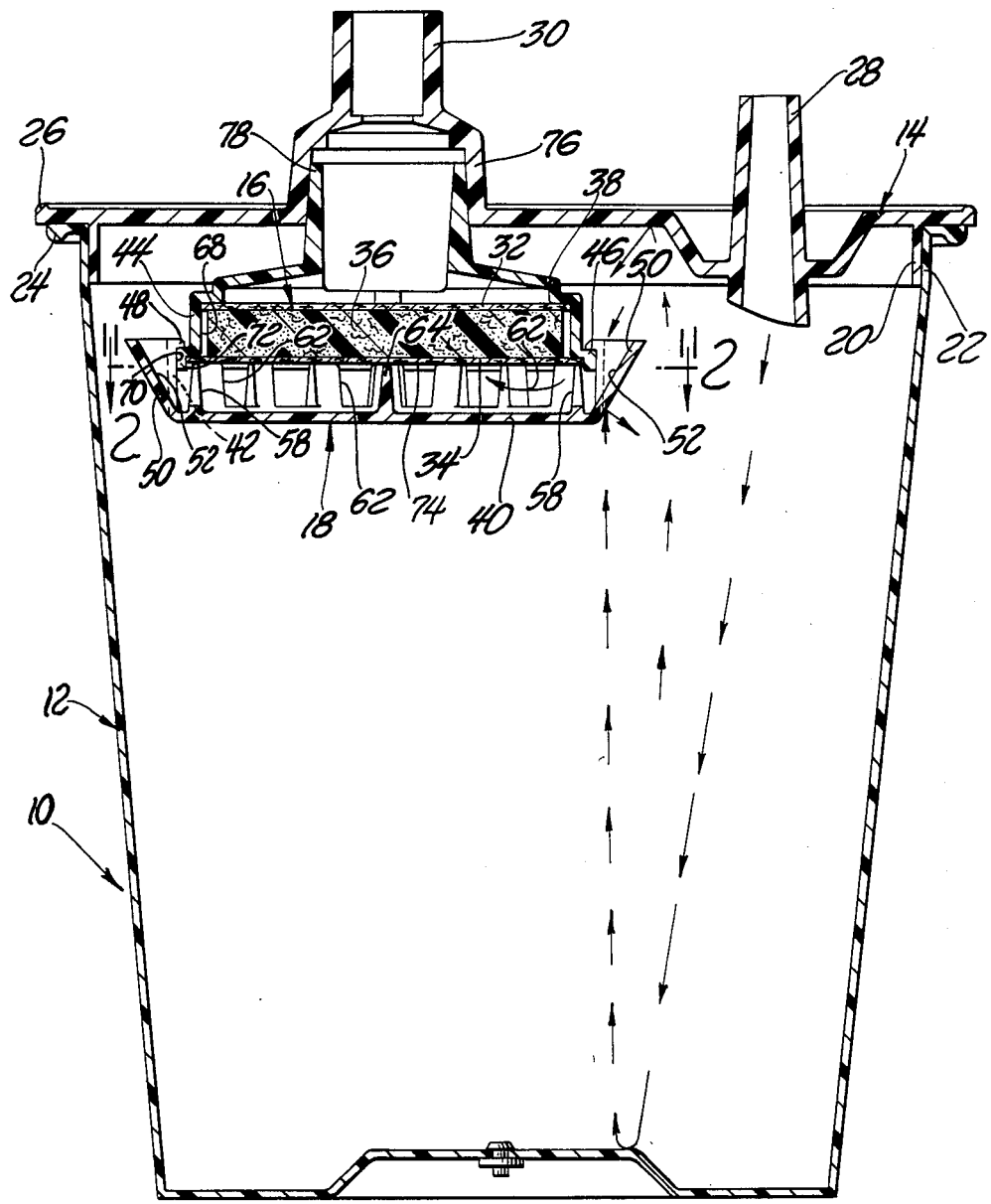
FIG. 1 is an elevational cross sectional view of a canister filter assembly constructed in accordance with the instant invention.

A canister filter assembly for use in a vacuum line for trapping particulates and liquids from liquid drawn through the vacuum line is generally shown at 10. The assembly 10 includes a cupped shaped container generally indicated at 12, a lid member generally indicated at 14, filter means generally indicated at 16, and filter support mean generally indicated at 18. The lid member 14 is disposed over the container 12 in sealing engagement therewith. The instant invention may be used with or adapted to various constructions of canister assemblies. In the preferred embodiment shown in FIG. 1, the lid member 14 includes an annular downwardly extending rim 20 force fit within the mouth portion 22 of the container 12. The container 12 includes an annular lip 24 disposed about the mouth portion 22 which further perfects the seal with the outwardly extending rim 26 of the lid member 14.

The lid member 14 further includes a fluid inlet 28, commonly referred to as a patient port. The fluid inlet 28 is in the form of a spout adapted to be connected to tubing or a connector member for receiving fluid therethrough. The fluid may be body fluids from a surgical site, or mucous material from a tracheal or nasal gastric passageway. The aspirate may include gases, particulates and aerosols. The aerosol is small droplets of the aspirate. The lid member 14 includes a fluid outlet, commonly referred to as vacuum port 30 adapted to be connected to tubing or a connector member for the outlet of gases to the vacuum pump. Canisters commonly used may include other ports, such as emptying ports or tandem or orthopedic ports having caps thereon and may be constructed in various configurations well known in the art.

The filter means 16 filters the particulates and liquids from the fluids passing through the fluid outlet 30. The filter means includes a hydrophobic filter membrane 32, a prefilter 34, and inert spacer material 36 disposed therebetween. The prefilter 34 filters out larger particulates and most aerosols. The hydrophobic filter membrane 32 prevents the passage of microscopic particulates from passing through the outlet port 30 while further functioning as a valve for preventing aqueous fluid from passing therethrough. Hence, the hydrophobic filter membrane 32 acts as the float member of prior art assemblies yet does not inherently have the problems of prior art float assemblies wherein the float would stick on its support or prematurely shut off fluid flow. The hydrophobic or "water hating" filter membrane 32 will prevent fluid from passing therethrough once the fluid level rises within the canister to a level above the filter support means 18. The prefilter 34 and hydrophobic filter 32 effectively prevents the passing of aerosols into the outlet 30 as well.

The filter support means 18 supports the filter means 16 within the fluid outlet 30. The filter support means 18 includes cover means spaced below the filter means 16 for forcing the flow of aerosols and fluids into the filter support means 18 downwardly away from the filter means 16 prior to flowing in the opposite direction through the filter means 16. More particularly, the filter support means 16 includes a filter holder 38. The cover means includes a cap member 40. The cap member 40 provides a bottom cover portion of the filter support means 18 spaced below the prefilter 34 of the filter means 16. The cap member 40 includes an upwardly extending peripheral rim 42 perfecting a seal with the filter holder 38. Specifically, the filter holder 38 includes a downwardly opening bowl shaped portion 44 having a peripheral outwardly extending lip 46. The rim 42 of the cap member 40 is outwardly deflectable and includes an inwardly extending flange 48 about the periphery thereof for engaging the peripheral lip 46 to attach the cap member 40 to the filter holder 38. The cap member 48 may be removed by manually deflecting the rim 42 to remove the filter means 16. The cap member 40 is snapped back on to the filter holder 38 to secure a new filter means 16 therein.

The rim 42 of the cap member 40 including outwardly extending louver portions 50 defining upwardly or sideways facing openings 52 proximate to the lid 14 to provide the tortuous path for the entrance of fluid flow into the filter support means 18. As shown by the arrows in FIG. 1, the louver portions 50 deflect fluid flow from directly entering the filter support means 18 thereby preventing direct impaction of aerosols and particulates against the filter means 16. As aerosols forced by inertia tend to travel in straight lines, and not around curves. The aerosol is deflected off of the louver portions 50 as indicated by the arrows in FIG. 1 and deflected downwardly. The louver portions 50 thereby provide a tortuous path presenting several bends for the fluid to travel. Such a path does not constrict the flow of gases to be exhausted but does tend to collect the aerosols and particulates against the walls of the tortuous path. This configuration minimizes aerosol assault on the filter means 16 thereby limiting direct contact of aerosols and particulates against the filter means 16. There is not direct flow of aerosols and particulates into the canister and directly onto the filter means 16.

Figure 2:
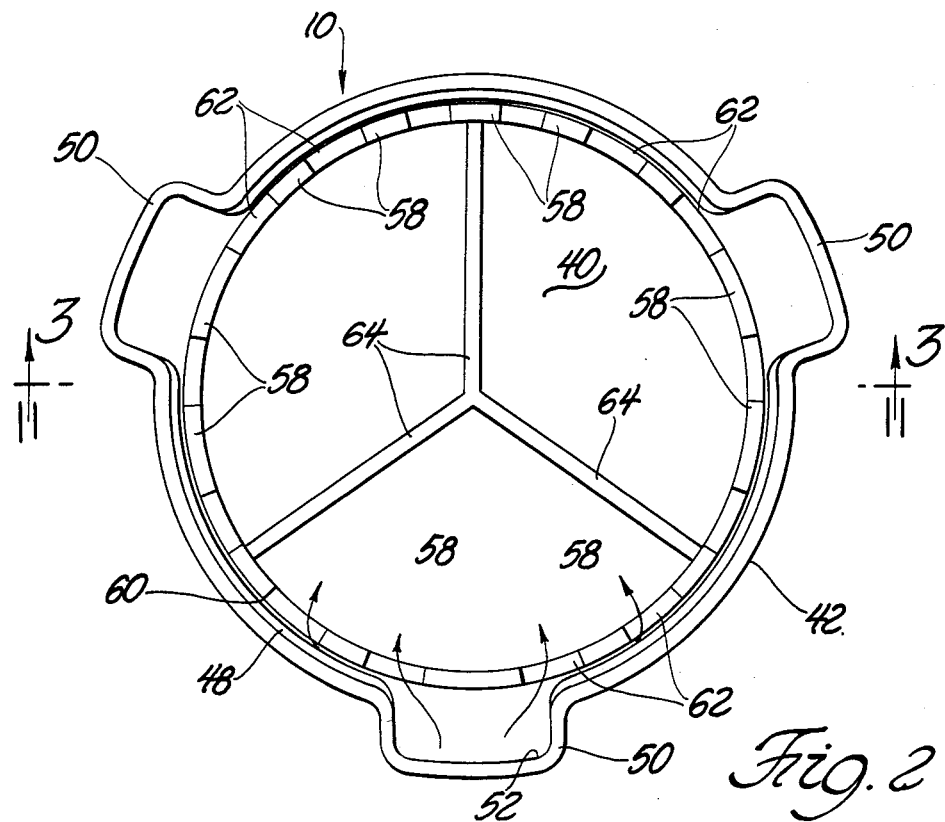
FIG. 2 is a plan view taken substantially along lines 2—2 of FIG. 1.
Figure 3:
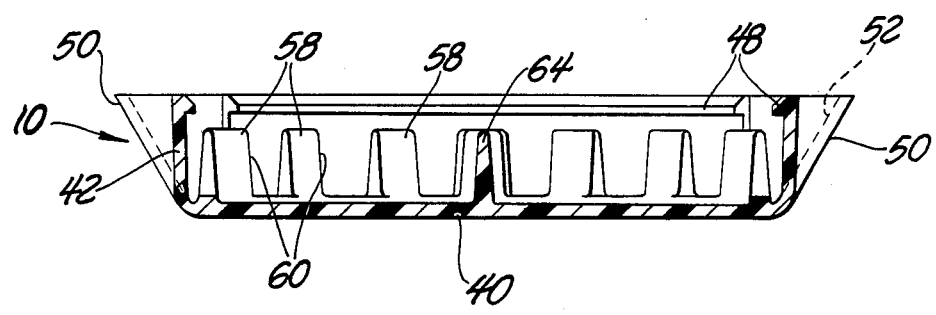
FIG. 3 is a cross sectional view taken substantially along lines 3—3 of FIG. 2.

The filter support means 18 includes an annular wall 58 extending between the cap member 40 and the filter means 16 defining an annular passageway 60 between the wall 58 and the rim 42. The flow of fluid through the passageway 60 is shown by the arrows in FIG. 2. The wall 58 has spaced openings 62 extending therethrough and closed wall portions 58 disposed directly within each of the louver portions 50 to further torture the fluid flow into the filter support means 18 as indicated by the arrows in FIG. 2. The tortuous path created by the instant invention provides for a build up of the aerosol and particulate matter about each bend in the tortuous, such as the louver openings 52 and the walls 58. Impaction of the particles against the filter means 16 is decreased as a significantly lessor amount of the particles reach the filter means 16. This significantly increases the useful life span of the filter assembly 10.

The cap member 40 defines chambers within the filter support means 18 and below the filter means 16 for isolating a plurality of different fluid flow paths through the filter support means 18 to isolate portions of the filter means 16. In particular, the filter support means 18 includes radially extending ribs 64 projecting upwardly from the cap member 40 to the filter means 16, abutting against the prefilter 34. The ribs 64 define the isolated chamber below the prefilter 34 for the flow of fluid therethrough.

The chamber design is directed to the problem of foaming within the assembly 10. Foaming is a function of air and liquid within the container 12. Under certain conditions, the foam may rise very quickly within the container 12. Unlike prior art assemblies wherein the foam would cause immediate shut off of the valve of the suction system, foam may enter the subject assembly 10 through one or two of the louver openings 52 but is retained within each of those chambers adjacent thereto by the ribs 64. The third chamber may still provide unobstructed and uncontaminated flow therethrough without contamination by the foam. As the cap member 40 protects the filter means 16 from splashing within the canister 12, the filter support means 18 provides an effective construction for effective unobstructed flow producing a minimum of flow resistance through the filter means 16.

The filter holder 38 extends downwardly from the lid 14 and includes seat means 68 for seating the filter means 16 within the filter holder 38.

The peripheral lip 46 of the filter holder 38 includes an annular downwardly extending flange 70 about the periphery thereof. The flange 70 has an inner surface defining a shoulder 72. The filter means 16 includes a bottom annular rim 74 extending radially outwardly therefrom and being clamped between the annular wall 58 of the cap member 40 and the shoulder 72. As shown in FIG. 1, the filter 34 includes the bottom annular rim 74 clamped between the annular wall 58 and the shoulder 72.

The fluid outlet 30 includes a recessed portion 76. The filter holder 38 includes a neck portion 78 above the filter means 16 for being operatively connected to the lid member 14 within the recessed portion 76. The recessed portion 76 has a smooth inner surface. The neck portion 78 has a smooth outer surface engaging the inner surface of the recessed portion 76. The filter support means 18 is an independent cartridge which can be removed from the lid member 14 by displacement of the neck portion 78 from the recessed portion 76 for cleaning or replacement of the filter means 16. Other methods of attaching the filter holder 38 to the lid member 14 may be used or the filter holder 38 may be an integral part of the canister.

The invention has been described in an illustrative manner, and it is to be understood that the terminology which has been used is intended to be in the nature of words of description rather than of limitation.

Obviously many modifications and variations of the present invention are possible in light of the above teachings. It is therefore, to be understood that within the scope of the appended claims wherein reference numerals are merely for convenience and are not to be in any limiting, the invention may be practiced otherwise that is specifically described.

What is claimed is:

1. A canister filter assembly (10) for use in a vacuum line for trapping particulates and liquids from fluid drawn through the vacuum line, said assembly (10) comprising: a container portion (12); a lid portion (14) disposed over said container portion (12) in sealing engagement therewith, said lid portion (14) including a fluid inlet (28) and a fluid outlet (30); filter means (16) for filtering the particulates and liquids from the fluids passing through said fluid outlet (30); and filter support means (18) for supporting said filter means (16) within said fluid outlet (30) and characterized by including cover means (40) spaced below said filter means (16) for forcing the flow of fluid into said filter support means (18) downwardly away from said filter means (16) prior to flowing in the opposite direction through said filter means (16).

2. An assembly as set forth in claim 1 further characterized by outwardly extending louver portions (50) defining upwardly facing openings (52) spaced from and proximate to said lid portion (14) to provide a tortuous path for the entrance of fluid flow into said filter support means (18).

3. An assembly as set forth in claim 2 further characterized by said filter support means (18) including a rim portion (42) extending upwardly from said cover means (40) and including said louver portions (50), said filter support means (18) further including an annular wall (58) extending between said cover portion (40) and said filter means (16) defining an annular passageway (60) between said wall (58) and said rim (42), said wall (58) having spaced openings (62) extending therethrough and closed wall portions (58) disposed directly within each of said louver portions (50) of said rim (46) to further torture the fluid flow into said filter support means (18).

4. An assembly as set forth in claim 3 further characterized by said cover means (40) defining chambers within said filter support means (18) and below said filter means (16) for isolating a plurality of different fluid flow paths through said filter support means (18) and said filter means (16).

5. An assembly as set forth in claim 4 further characterized by said filter support means (18) including radially extending ribs (64) projecting upwardly from said cover means (40) to said filter means (16) and defining isolated chambers below said filter means (16) for the flow of fluid therethrough.

6. An assembly as set forth in claim 4 further characterized by said filter support means (18) including a filter holder (38) extending downwardly from said lid portion (14) and including seat means (68) for seating said filter means (16) within said filter holder (38), said filter support means (18) further including a cap member (40) operatively connected to said filter holder (38) and defining said cover means for retaining said filter means (16) within said seat means.

7. An assembly as set forth in claim 6 further characterized by said filter holder (38) including a downwardly opening bowl shaped portion (44) having a peripheral lip (46), said rim (42) of said cap member (40) being outwardly deflectable and including an inwardly extending flange (48) about the periphery thereof for engaging said peripheral lip (46) to attach said cap member (40) to said filter holder (38).

8. An assembly as set forth in claim 7 further characterized by said peripheral lip (46) of said filter holder (38) including an annular flange (70) extending downwardly from the periphery thereof and having an inner surface defining a shoulder (72), said filter means (14) including a bottom annular rim (74) extending radially outwardly therefrom and being clamped between said annular (54) of said cap member (40) and said shoulder (72).

9. An assembly as set forth in claim 8 further characterized by said filter means including a hydrophobic filter member (32).

10. An assembly as set forth in claim 9 further characterized by said filter means including a prefilter spaced from and disposed below said hydrophobic filter member.

11. An assembly as set forth in claim 8 further characterized by including inert spacer material (36) between said hydrophobic filter and said prefilter.

12. An assembly as set forth in claim 11 further characterized by said prefilter (34) including said bottom annular rim (74) clamped between said annular wall (58) of said cup member (34) and said shoulder (72).

13. An assembly as set forth in claim 4 further characterized by said fluid outlet (30) including a recessed portion (76), said filter support means (18) including a neck portion (78) above said filter means (16) for being operatively connected to said lid portion (14) within said recessed portion (76).

14. An assembly as set forth in claim 13 further characterized by said recessed portion (76) having a smooth inner surface, said neck portion (78) having a smooth outer surface engaging said inner surface of said recessed portion (76).

15. An assembly as set forth in claim 1 further characterized by said filter means (16) including a hydrophobic filter member (32).

16. An assembly as set forth in claim 15 further characterized by said filter means (16) including a prefilter (34) spaced from and disposed below said hydrophobic filter member (32).

17. An assembly as set forth in claim 16 further characterized by including inert spacer material (36) between said hydrophobic filter member (32) and said prefilter (34).

18. An assembly as set forth in claim 1 further characterized by including means for shutting off fluid flow through said fluid outlet (30) upon filling of fluid in said canister (12).

19. An assembly as set forth in claim 18 further characterized by said means including a hydrophobic filter member (32) disposed over said fluid outlet (30).

20. A filter assembly (18) to be mounted in the fluid outlet (30) of a canister assembly (10) for use in a vacuum line for trapping particulates and liquids from fluid drawn through the vacuum line, said assembly (18) comprising: filter means (16) having an inlet side and an outlet side for filtering the particulates and liquids from fluids passing therethrough, and filter support means (18) having an inlet end (28) and an outlet end adapted to be mounted within the fluid outlet (30) of the canister (12), said filter support means (18) including cover means (40) on said fluid inlet side of said filter means (16) and spaced therefrom below said filter means (16) for forcing the flow of fluid into said filter support means (18) downwardly away from said filter means (16) prior to flowing in the opposite direction through said filter means (16).

21. An assembly as set forth in claim 20 further characterized by said cover means (40) including outwardly extending louver portions (50) defining upwardly facing openings (52).

22. An assembly as set forth in claim 21 further characterized by said filter support means (18) including a rim portion (42) extending upwardly from said cover means (40) and including said louver portions (50), said filter support means (18) further including an annular wall (58) extending between said cover means (40) and said filter means (16) defining an annular passageway (60) between said wall (58) and said rim (42), said wall (58) having spaced openings (62) extending therethrough and closed wall portions (58) disposed directly within each of said louver portions (50) of said rim (46) to further torture the fluid flow into said filter support means (18).

23. An assembly as set forth in claim 22 further characterized by said cover means (40) defining chambers within said filter support means (18) and below said filter means (16) for isolating a plurality of different fluid flow paths through said filter support means (18) and said filter means (16).

24. An assembly as set forth in claim 23 further characterized by said filter support means (18) including radially extending ribs (64) projecting upwardly from said cover means (40) to said filter means (16) and defining isolated chambers below said filter means (16) for the flow of fluid therethrough.

25. An assembly as set forth in claim 22 further characterized by said filter means (16) including a hydrophobic filter member (32).

26. An assembly as set forth in claim 25 further characterized by said filter means (16) including a prefilter (34) spaced from and disposed below said hydrophobic filter member (32).

27. An assembly as set forth in claim 26 further characterized by including inert spacer material (36) between said hydrophobic filter membrane (32) and said prefilter (34).

* * * * *